United States Patent [19]

Perlin

[11] Patent Number: 4,815,466

[45] Date of Patent: Mar. 28, 1989

[54] SURGICAL CLIP

[76] Inventor: Alfred R. Perlin, 3382 Dato Ave., Highland Park, Ill. 60035

[21] Appl. No.: 523,270

[22] Filed: Aug. 15, 1983

Related U.S. Application Data

[63] Continuation of Ser. No. 429,170, Sep. 30, 1982, Pat. No. 4,556,060.

[51] Int. Cl.⁴ ............................................. A61B 17/12
[52] U.S. Cl. .................................... 128/325; 128/346; 251/10
[58] Field of Search ............... 128/346, 321, 322, 325; 251/10; 81/425 R, 425 A, 426, 428 R

[56] References Cited

U.S. PATENT DOCUMENTS

| | | | |
|---|---|---|---|
| 2,137,710 | 11/1938 | Anderson | 128/321 |
| 3,279,479 | 10/1966 | Solomon | 128/321 X |
| 3,326,217 | 6/1967 | Kerr | 128/325 |
| 3,367,337 | 2/1968 | Javna et al. | 128/325 |
| 3,446,211 | 5/1969 | Markham | 128/322 |
| 3,868,957 | 3/1975 | Doddington | 128/346 |
| 4,106,508 | 8/1978 | Berlin | 128/346 |
| 4,324,248 | 4/1982 | Perlin | 128/346 X |
| 4,337,774 | 7/1982 | Perlin | 128/346 X |

*Primary Examiner*—Michael H. Thaler

[57] ABSTRACT

A surgical clip comprises a body with two initially disconnected arms. Each arm terminates in an integral outwardly projecting clamping jaw. One of the arms includes a passageway through which the other arm is inserted to align the arms and to position the jaws in aligned mutual juxtaposition. A mating section is formed on one of the arms and is adapted to interconnect with a reciprocal mating section on the other arm to complete assembly of the clip.

3 Claims, 3 Drawing Sheets

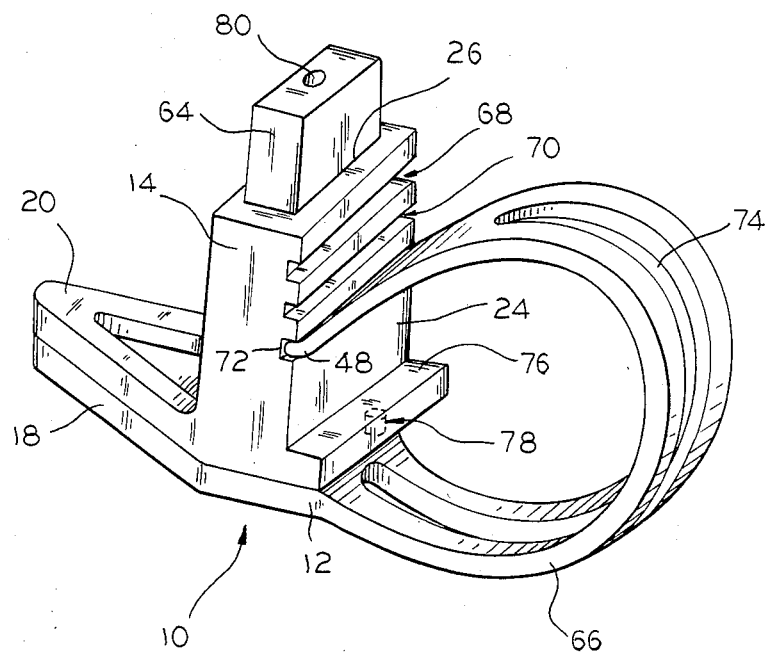
FIG. 11
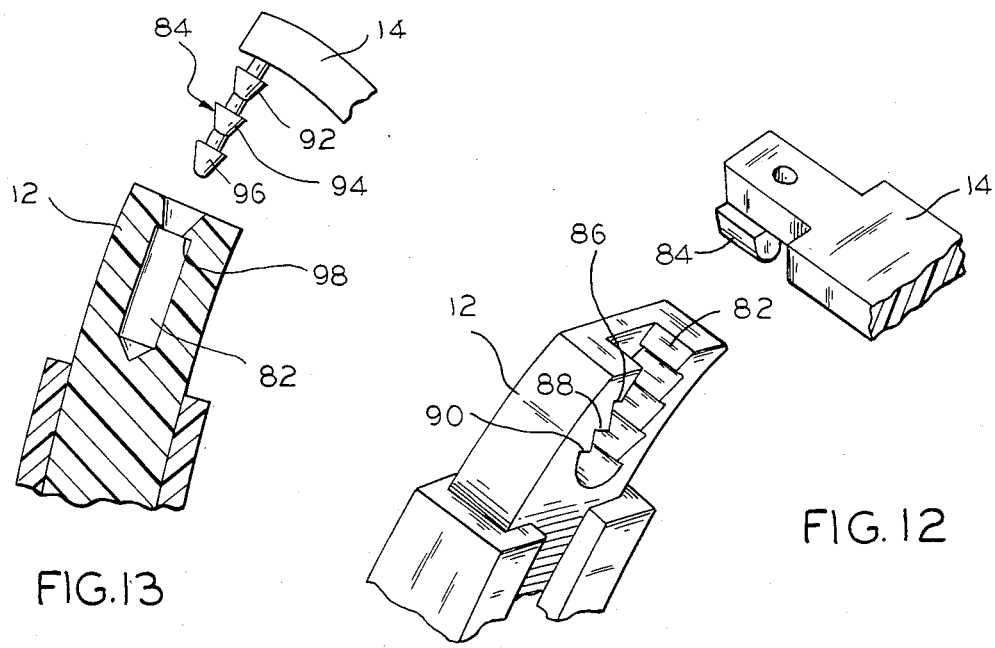
FIG. 12
FIG. 13

SURGICAL CLIP

CROSS-REFERENCE TO RELATED APPLICATION

This application is a continuation-in-part of my copending U.S. patent application Ser. No. 429,170, filed Sept. 30, 1982, U.S. Pat. No. 4,556,060.

BACKGROUND OF THE INVENTION

This invention relates generally to surgical clips and, more particularly, to clips for temporarily occluding blood vessels during surgery.

A wide variety of surgical clips have been proposed heretofore for purposes of vascular occlusion. However, many of these clips have been constructed in a manner such that they directly squeeze or pinch the vessel closed between opposing and converging flat surfaces. The clamping action of these prior clips necessarily gives rise to the possibility of damage or rupture of the vessel as a result of their intrusive pinching or crushing effect on the clamped vessel. Other clips, as exemplified by the clips described in U.S. Pats. Nos. 3,996,937 and 4,024,868, have been constructed to avoid this pinching or crushing action on the vessel. However, these clips are designed to cause permanent occlusion and are not suitable for temporary occlusion in view of the closure action of the metallic rod-like clamping members which exert relatively high pressure on the clamped vessels and cause complete collapse of the vessel walls.

Thus, it has been a continuing problem in the design of surgical clips to develop a clip for the temporary occlusion of blood vessels which is effective in stopping blood flow without causing permanent occlusion or present risk of traumatic damage to the vessel.

A further problem which has been encountered with prior surgical clips is that they have been manufactured and stored in a stressed condition. Over a period of time, such devices lose their elasticity and upon application may not provide the necessary clamping force or pressure to occlude a vessel and, if sufficient pressure is not exerted, the potential exists for slippage or disengagement of the clip from the vessel.

SUMMARY OF THE INVENTION

The present invention is directed to an improved surgical clip particularly adapted for the clamping of blood vessels. The clip preferably has a body construction of a suitable springy material such as acetal, polyethylene, polypropylene or like plastic materials.

The body includes two initially disconnected arms with each arm terminating at one end in an outwardly projecting clamping jaw. One of the arms has a passageway included therein through which the other arm is inserted in a manner such that the arms are properly aligned and the jaws on the ends of the arms are thereby positioned to extend outwardly therefrom in mutual juxtaposition. Furthermore, one of the arms has a connecting or mating section adapted for interconnection with a reciprocal connecting or mating section on the other arm at a position remote from the jaw end thereof so that the arms can be joined to complete assembly of the clip.

In an unassembled state, the clip can be stored in an unstressed condition, for example, with one arm of the body inserted into the passageway in the other body arm and with the jaws properly aligned and the clip can be readily assembled into an operational condition by merely joining or interconnecting the arms whenever desired. In assembly, the jaws are positioned to be opened to receive or remove a member such as a blood vessel as a result of movement of the joined or interconnected arms and to be clampingly closed about the vessel in response to an oppsoite movement of the arms.

The jaws are formed and positioned to provide a reverse curve or S-shaped clamping path for the vessel so that occlusion of blood flow can be accomplished with minimal applied clamping force or pressure thereby reducing the potential for damage of the clamped vessel. Ideally, this clamping force or pressure should approximate the systolic pressure in the vessel normally in the range of about 100 to 300 mm Hg., in order to temporarily stop the flow of blood therein without causing potential damage to the vessel.

Furthermore, with regard to the clamping force, in a preferred embodiment of this invention, the clips have been designed so that the pressure which the clips will exert on the clamped member, such as a blood vessel, can be preselected or adjusted during use based on the manner of adjustable interconnection of the clip arms. Thus, for example, different clamping forces can be present to accommodate vessels having varying circumferential dimensions. Also, to enable reutilization of the clips over an extended period of time, the clamping force can be adjusted to provide an effective but not harmful degree of pressure for temporary occlusion of a vessel even though the elasticity of the structural material used in forming the clip has declined due to prior usage.

It is, therefore, an object of the invention to provide an improved surgical clip particularly adapted for clamping blood vessels.

It is a further object to provide a surgical clip adapted to be stored in an unstressed condition which can be readily assembled for use during surgery.

Another object is to provide a surgical clip which is effective for the occlusion of blood vessels but is not harmful to a clamped vessel.

A still further object is to provide a surgical clip which exerts a predetermined clamping force on a vessel sufficient to temporarily occlude the vessel without causing permanent occlusion thereof.

BRIEF DESCRIPTION OF THE DRAWINGS

The foregoing and other objects and advantages of this invention will become more readily appreciated as the same becomes completely understood by reference to the following detailed description when taken in conjunction with the accompanying drawings wherein:

FIG. 11 is a perpective view of another surgical clip of this invention in a fully assembled rest position;

FIG. 12 is a partial perspective view of a locking arrangement utilizable in the clips of the present invention to provide a selectable and adjustable interconnection of the clip arms; and FIG. 13 is a partial perspective view of another selectable and adjustable locking arrangement for the inventive clips.

DETAILED DESCRIPTION

Figure 1:
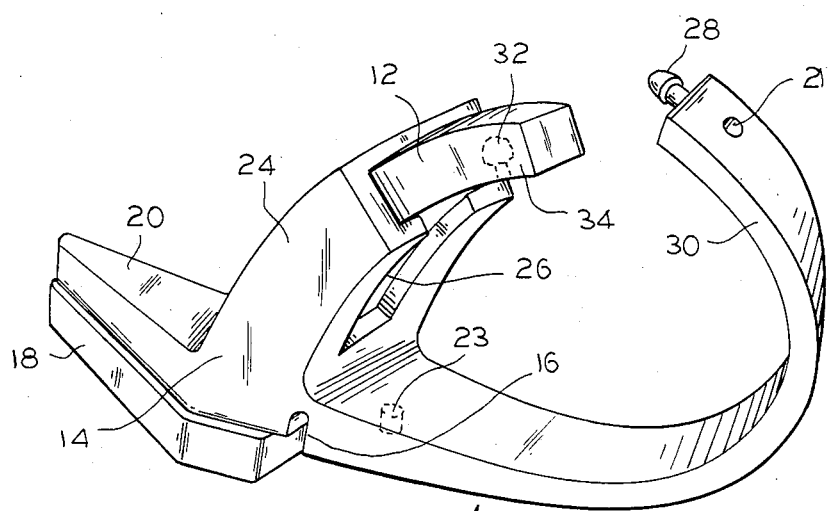
FIG. 1 is a perspective view of a partially assembled surgical clip in accordance with the present invention.

A description of the invention follows referring to the drawings in which like reference numerals denote like elements of structure in each of the several figures.

Referring now to FIG. 1 there is shown generally at 10 a surgical clip body in a partially assembled, unstressed condition suitable for storage. The clip body 10 may be provided in a number of lengths and widths, however, the comparative shapes and relationship of components parts thereof are generally maintained. Clip 10 includes arms 12 and 14 with arm 14 including a housing section 24 formed to provide a passageway 26 through which arm 12 is inserted in order to properly align arms 12 and 14 and, also, the clamping jaws 18 and 20 which are formed integral with and project outwardly from a first end of arms 12 and 14, respectively. The clip 10 including both arms 12 and 14 and jaws 18 and 20 preferably is molded of a springy material such as nylon or a suitable flexible but somewhat rigid plastic material such as acetal, polyethylene, polypropylene or the like.

Figure 3:
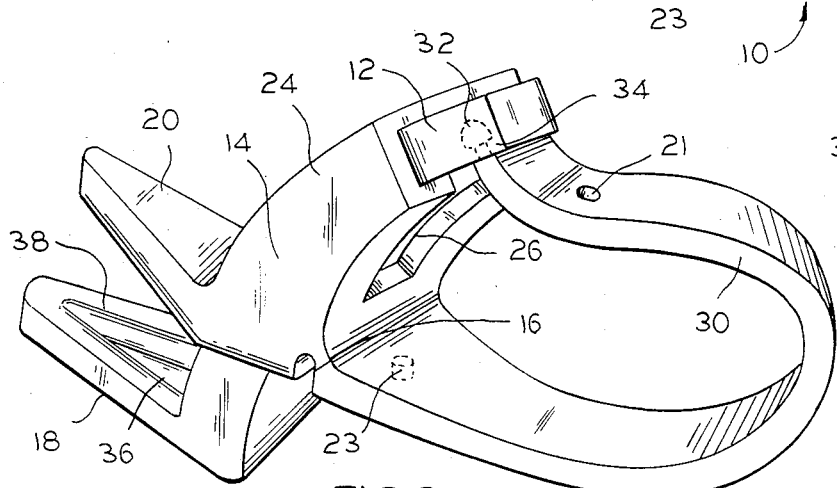
FIG. 3 is a perspective view of the surgical clip of FIG. 1 in a fully assembled open position to receive a vessel.

As best seen in FIG. 3, the jaw 18 includes a longitudinally extending slot 36 which tapers inwardly lengthwise of jaw 18. Jaw 20 is cooperatively tapered longitudinally in a manner such that the jaws 18 and 20 are adapted to be nestingly engaged when clip 10 is assembled.

Assembly of clip 10 is readily accomplished by interconnecting or joining a male snap locking member 28 formed integral with and extending outwardly from a tail section 30 of arm 14 with a reciprocal female locking member 32 positioned at a mating section 34 of arm 12. Upon completion of this interconnection of locking members 28 and 32, the tail section 30 of arm 14 is essentially formed into a loop with jaws 18 and 20 extending outwardly from arms 12 and 14, respectively in mutual juxtaposition as clearly shown in FIG. 2. To further facilitate assembly of the clip 10, integral hinge 16 may be provided, if desired. Hinge 16 is an integral or living hinge defined by a tapered, rounded or ridged undercut in arm 14 intermediate housing section 24 and tail section 30 and functions to facilitate movement of tail section 30 into position for interconnection with arm 12.

Figure 2:
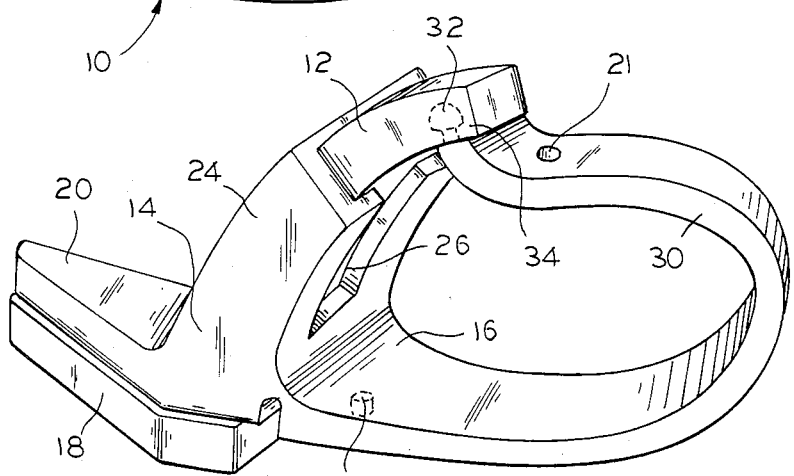
FIG. 2 is a perspective view of the surgical clip of FIG. 1 in a fully assembled rest position.

FIG. 3 illustrates clip 10 in a fully assembled open position to accommodate a blood vessel interposed between jaws 18 and 20. Opening of jaws 18 and 20 from their closed rest position as shown in FIG. 2 is accomplished by manually compressing the opposing surfaces of the looped tail section 30 of arm 14 towards one another either by pressure exerted by fingers grasping clip 10 or by a suitable delivery tool (not shown), utilizing applicator wells 21 and 23, with sufficient force to overcome the bias of the springy material which urges interconnected arms 12 and 14 apart and concomitantly the jaws 18 and 20 into the closed or rest condition. Thus, by overcoming the spring bias of the material of which the clip 10 is formed, the jaw 18 is urged downwardly and the jaw 20 is urged upwardly to provide an opening to accommodate a blood vessel interposed between the jaws 18 and 20. In order to clampingly engage the interposed vessel the compressive pressure on arms 12 and 14 is released and the aforementioned inherent bias will cause the jaws 18 and 20 to close in order to clamp or occlude vessel 32 in a manner shown in FIGS. 4 and 5.

Figure 4:
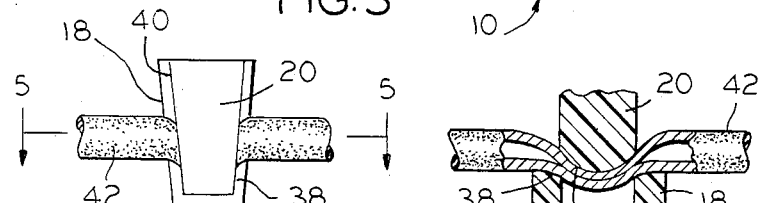
FIG. 4 is a plan view of the jaws of the surgical clip of FIG. 1 in a closed position clamped on a vessel.
Figure 5:
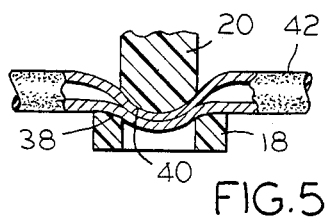
FIG. 5 is a cross-sectional view taken at line 5—5 of FIG. 4.

When jaws 18 and 20 are in a fully assembled closed position, jaw 20 is disposed lengthwise of slot 36 and is substantially centered between lateral edges 38 of slot 36 with lateral edges 40 of jaw 20 abutting in nesting engagement with lateral edges 38. Preferably, the lateral edges 38 and 40 are conformably tapered or rounded and most preferably are elliptically shaped in cross-section, to provide this nesting engagement. Thus, as shown in FIGS. 4 and 5, when a blood vessel 42 is interposed between jaws 18 and 20, a reverse curve or S-shaped clamping path is provided for vessel 42 with the tapered or rounded edges 38 of slot 36 in conjunction with the conformably tapered or rounded edges 40 of jaw 20 applying a uniformly distributed pressure against the opposing lateral sides of the vessel 42 to accomplish occlusion thereof. It should be noted that in view of the tapered construction of edges 38 and 40 no sharp surfaces are in contact with vessel 42 as the clamping force is applied. Accordingly, the potential for damage or pinching of the vessel 42 is greatly diminished. Furthermore, as a result of the application of uniformly distributed pressure at a plurality of sealing points along the clamping path for vessel 42, the occlusive action of the jaws 18 and 20 can be accomplished with a minimum of pressure to achieve effective temporary stoppage of blood flow without causing permanent occlusion thereof.

Figure 7:
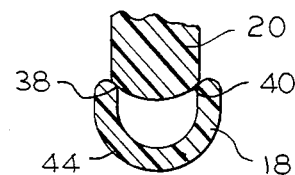
FIG. 7 is a sectional view of the jaws of the surgical clip in a fully assembled rest position employing the jaw of FIG. 6.
Figure 6:
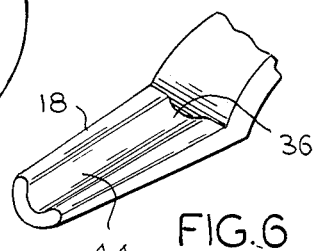
FIG. 6 is a partial perspective view of an alternate embodiment of a jaw of the surgical clip of FIG. 1.

In FIG. 6, an alternative embodiment of the jaw 18 is shown. In this embodiment of the jaw, a web or cradle 44 is formed to provide a trough for supporting an interposed vessel. The web 44 extends at least partially coextensive with the length of slot 36. The length of web 44 and the positioning thereof along the length of slot 36 is not critical so long as it is sufficient to accommodate the vessel being occluded by the clip. As illustrated in cross-section in FIG. 7, the jaw 18 and jaw 20 are shown in a fully assembled, rest position prior to the interposition and clamping of a vessel therebetween. It will be seen that the lateral edge of jaw 18 and the lateral edge 38 of the slot 36 are conformably tapered and abut in nesting engagement. Thus, in operation, when the jaws 18 and 20 are moved into an open position, a vessel is inserted therebetween and will be supported by the web 44 as the jaws 18 and 20 are moved back together into a closed, clamping position about the vessel.

Figure 8:
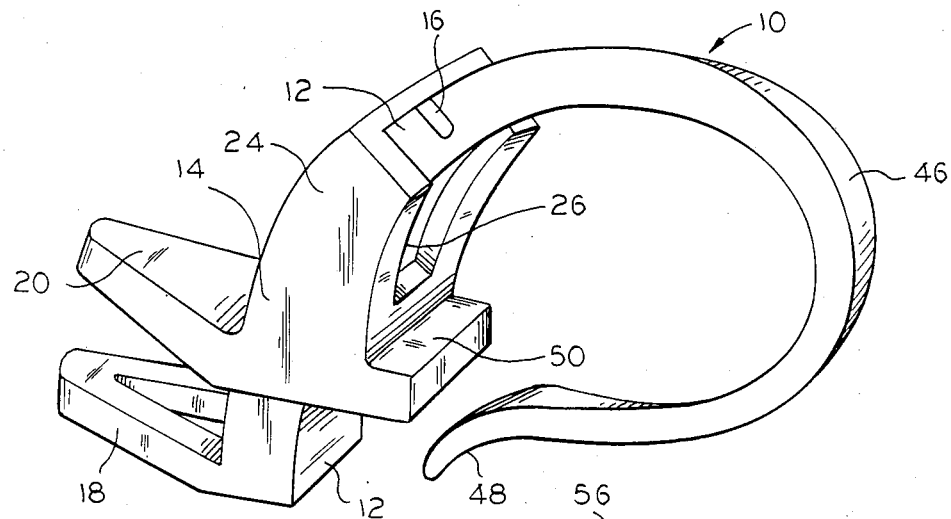
FIG. 8 is a perspective view of another embodiment of the surgical clip of the present invention.

FIG. 8 shows another embodiment of a surgical clip 10 in accordance with the present invention wherein clip body 10 includes arms 12 and 14 with integral jaws 18 and 20, respectively, projecting outwardly therefrom. Arm 14 includes a housing section 24 formed to provide a passageway through which arm 12 is inserted for purposes of aligning the arms 12 and 14 and their respective jaws 18 and 20. Arm 12 includes an integral tail section 46 hingedly joined to the section of arm 12 inserted through passageway 26 at a first end by an integral or living hinge 16 and which terminates at a second end remote from the first end in a hooked section 48 which is adapted to engage a shelf-like mating section 50 of arm 14 to detachably lock or join arms 12 and 14 with tail section 46 essentially formed into a looped configuration. Thus, the clip 10 can be stored in an unstressed condition and can be readily assembled into an operative condition merely by moving the hooked section of arm 12 into locking engagement with the shelf-like section 50 of arm 14. In this operative condition with arms 12 and 14 are joined and jaws 18 and 20 extending therefrom in aligned mutual juxtaposition, the jaws 18 and 20 can be opened to accommodate a blood vessel by applying compressive force on the opposing surfaces of looped tail section 46 either by pressure exerted by fingers grasping clip 10 or by a suitable delivery means so as to overcome the inherent closing bias exerted on jaws 18 and 20 by the interconnected arms 12 and 14 in the same manner as hereinbefore discussed with regard to the clip embodiment shown in FIGS. 1-3.

Figure 9:
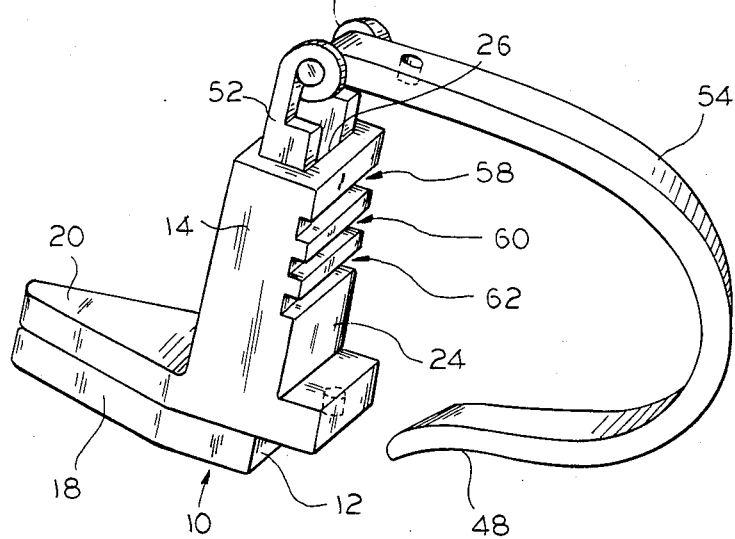
FIG. 9 is a perspective view of a further embodiment of the surgical clip of the present invention in a partially assembled condition with the clip jaws in a closed position.
Figure 10:
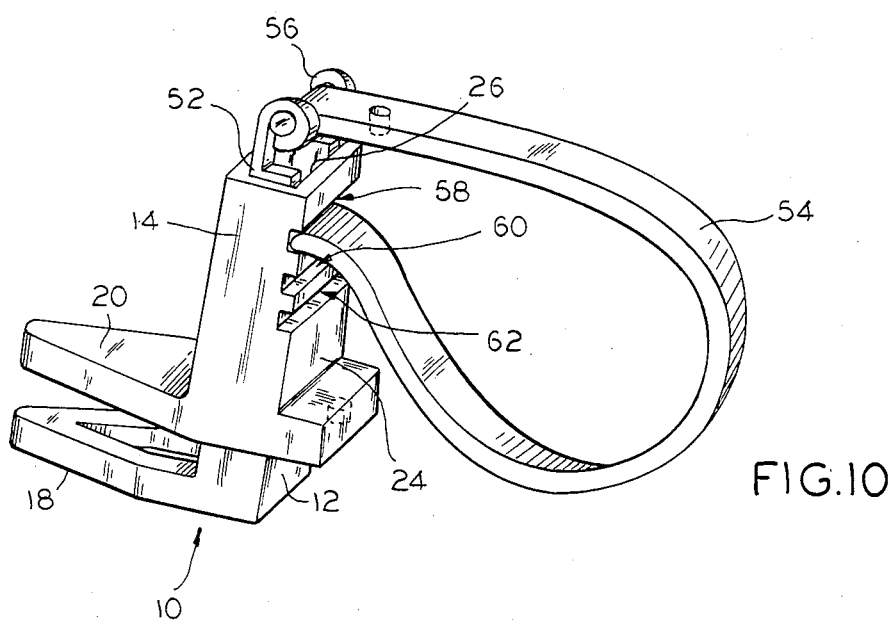
FIG. 10 is a perspective view of the surgical clip of FIG. 9 in a fully assembled open position.

FIGS. 9 and 10 show a further embodiment of a surgical clip 10 in accordance with the present invention wherein clip body 10 includes arms 12 and 14 with arm 12 having a first section 52 and a second section 54 hingedly joined by a pin and socket hinge assembly 56. Arm 14 includes a housing section 24 formed to provide a passageway 26 through which first section 52 of arm 12 is inserted in order to properly align the arms 12 and 14 and their respective jaws 18 and 20. The second section 54 of arm 12 terminates at its end remote from hinge assembly 56 in a hooked section 48 which is adapted to engage with any of the mating indentations or catches 58, 60 and 62 formed in the surface of housing 24 whereby arm 14 can be detachably interconnected with the second section of arm 12. Thus, in order to complete assembly of the clip 10, the hooked section 48 of arm 12 acting as the male member is interconnected with a selected one of the mating indentations or female members 58, 60 or 62 to lockingly engage arms 12 and 14 with the second section of arm 12 essentially formed into a loop. In operation then, the jaws 18 and 20 of the fully assembled clip 10 can be moved from their closed rest position to an open position to accommodate an interposed vessel as shown in FIG. 10 by compressing the opposing surfaces of looped second section 54 toward one another which will overcome the inherent closing bias on the jaws and move them to an open position to accept a vessel whereafter release of the compressive force on the loop will allow the jaws to clampingly close about the interposed vessel.

As will be noted with regard to the clip 10 shown in FIGS. 9 and 10, the amount of clamping force which the clip 10 will exert is dependent upon the particular mating indentation 58, 60 or 62 which is selected for engagement with hooked section 48 of arm 12 and, in view of the detachable nature of the interconnection between hooked section 48 the selected indentation 58, 60 or 62, the clamping force as well as the jaw opening dimension can be readily adjusted by moving the hooked section 48 from one indentation to another in a ratchet-like manner. Accordingly, the clip 10 of this embodiment is constructed in a manner such that the pressure which the clip will exert can be preselected based on the choice of mating indentation to be interconnected with arm 12 and, also, provides a adjustability feature if a different pressure is desired at any time.

Another embodiment of the clip 10 of this invention is shown in FIG. 11 wherein clip body 10 includes arms 12 and 14 with integral jaws 18 and 20, respectively, projecting outwardly therefrom. Arm 14 includes a housing section 24 formed to provide a passageway 26 through which a first section 64 of arm 12 is inserted for purposes of aligning arms 12 and 14 and their respective jaws 18 and 20. Arm 12 includes an integral tail section 66 extending rearwardly from a position at the intersection of first section 64 of arm 12 and jaw 18 and terminates at a position remote therefrom in a male hooked section 48. Hooked section 48 is adapted to engage with any of female mating indentations or catches 68, 70 and 72 formed in the surface of housing 24 whereby arms 12 and 14 can be detachably interconnected to complete assembly of clip 10 in the same manner as discussed hereinbefore with regard to the embodiment of this invention illustrated in FIGS. 9 and 10. As will be noted tail section 66 of arm 12 includes an intermediate longitudinally extending slot 74 which is provided to facilitate bending and movement of arm 12 essentially into a loop for engagement and interconnection with mating indentations 68, 70 or 72 on arm 14. In its fully assembled condition with arms 12 and 14 interconnected, for example, by engagement of hooked section 48 with mating indentation 72 as illustrated in FIG. 11, the clip 10 can be operated to open and shut jaws 18 and 20 for purposes of clamping a vessel interposed therebetween by applying compressive force on the looped tail section 66 as discussed hereinbefore. Alternatively, the jaws 18 and 20 may be manipulated into an open position by simultaneously applying compressive force on the free terminal stem end of the first section 64 of arm 12 and on step 76 of arm 14 and can be closed by releasing this force. To accommodate use of a suitable delivery tool for applying the noted compressive force on the first section 64 and on step 76, applicator wells 78 and 80 are provided therein with well 78 being accessible to the tool through slot 74 in arm 12.

FIGS. 12 and 13 illustrate further locking arrangements which can be utilized in conjunction with any of the embodiments of the clip 10 of this invention to provide the previously discussed preselection and adjustability features. As shown in FIG. 12, arm 12 includes a female receptable area 82 which is adapted for engagement with a reciprocal male element 84 depending from arm 14 in a manner such that element 84 will interconnect with any of steps 86, 88 or 90 of receptable 82 to provide a selectable, adjustable joinder between arms 12 and 14. FIG. 13 shows a further variation of a locking arrangement which may be employed in the clips of the invention wherein arm 12 is again provided with a female receptable area 82 which is adapted for engagement with a reciprocal male element 84 on arm 14. In this arrangement, the male element 84 includes serial frusto-conic sections 92, 94 and 96 which can engage with shoulder 98 in receptable 82 to lockingly join arms 12 and 14 in a selectable and adjustable manner.

However, as will be appreciated by those skilled in the art, although specific interconnecting arrangements are illustrated herein, the particular locking arrangement to be employed for interconnection of arms 12 and 14 is not critical and any of a variety of known interconnecting techniques and assemblies may be utilized for purposes of accomplishing this interconnection or joinder between the arms. Additionally, it should be recognized that the location of the mating section on one arm and the positioning of the reciprocating interconnection portion on the other arm may be selected at the option of the clip designer.

The forms of this invention illustrated and described herein are but preferred embodiments of these teachings in the forms currently preferred for manufacture. They are shown as illustrations of the inventive concepts, however, rather than by way of limitation, and it is pointed out that modifications and alterations may be indulged in within the scope of the appended claims.

What is claimed is:

1. A surgical clip comprising disconnected first and second arms of finite length, said first arm terminating at one end in an outwardly projecting first clamping jaw and said second arm terminating at one end in an outwardly projecting second clamping jaw, said first arm including a passageway through which said second arm is inserted to align said arms and to position said first and second jaws in mutual juxtaposition, said first and second arms including means formed integrally with said arms for detachably interconnecting said arms at a position remote from said jaw ends of said arms to form a unitary clip body with said jaws biased into engagement and with said first and second arms being movably operable to move said first and second jaws from engagement into an open position, said means for interconnecting said arms comprises a mating section formed in said first arm and a reciprocal mating section formed in said second arm adapted for detachable joinder of said arms whereby the pressure which the clip will exert on a clamped member can be preselected or can be adjusted during use of the clip.

2. A surgical clip comprising disconnected first and second arms of finite length, each of said arms including an integral clamping jaw, means for aligning said arms so that said jaw of said first arm is aligned in mutual juxtaposition with the jaw of said second arm and means integral with said arms for detachably interconnecting said first and second arms to bias said jaw of said first arm into engagement with said jaw of said second arm and to render said first and second arms operable to move said first and second jaws from engagement into an open position, said means for detachably interconnecting said arms includes means for adjusting the position of interconnection of said arms in order to adjust the pressure which the clip will exert on a clamped member.

3. A surgical clip comprising disconnected first and second arms of finite length, each of said arms including an integral clamping jaw, means for aligning said arms so that said jaw of said first arm is aligned in mutual juxtaposition with the jaw of said second arm and means integral with said arms for detachably interconnecting said first and second arms to bias said jaw of said first arm into engagement with said jaw of said second arm and to render said first and second arms operable to move said first and second jaws from engagement into an open position, said means for detachably interconnecting said arms includes means for adjusting the position of interconnection of said arms in order to adjust the pressure which the clip will exert on a clamped member, said means for adjusting the position of interconnection of said arms comprises multiple mating sections formed in at least one of said arms which can be selectively engaged by a mating section in the other of said arms.

* * * * *